US011491343B2

(12) United States Patent
Saitoh et al.

(10) Patent No.: US 11,491,343 B2
(45) Date of Patent: Nov. 8, 2022

(54) COIL APPARATUS FOR USE IN TRANSCRANIAL MAGNETIC STIMULATION APPARATUS PROVIDED WITH WOUND-WIRE COIL DISPOSED ON OR NEAR HEAD SURFACE

(71) Applicants: THE UNIVERSITY OF TOKYO, Tokyo (JP); OSAKA UNIVERSITY, Suita (JP)

(72) Inventors: Youichi Saitoh, Ikeda (JP); Masaki Sekino, Tokyo (JP); Keita Yamamoto, Tokyo (JP)

(73) Assignees: THE UNIVERSITY OF TOKYO, Tokyo (JP); OSAKA UNIVERSITY, Osaka (JP)

( * ) Notice: Subject to any disclaimer, the term of this patent is extended or adjusted under 35 U.S.C. 154(b) by 238 days.

(21) Appl. No.: 16/842,124

(22) Filed: Apr. 7, 2020

(65) Prior Publication Data
US 2020/0230431 A1 Jul. 23, 2020

Related U.S. Application Data

(62) Division of application No. 15/563,044, filed as application No. PCT/JP2016/060492 on Mar. 30, 2016, now abandoned.
(Continued)

(51) Int. Cl.
*A61N 2/02* (2006.01)
*A61N 1/40* (2006.01)
(Continued)

(52) U.S. Cl.
CPC .............. *A61N 2/02* (2013.01); *A61B 5/6803* (2013.01); *A61F 2/04* (2013.01); *A61N 1/40* (2013.01); *A61N 2/006* (2013.01)

(58) Field of Classification Search
CPC .................................................. A61N 2/00–12
See application file for complete search history.

(56) References Cited

U.S. PATENT DOCUMENTS

| 2004/0078056 A1 | 4/2004 | Zangen et al. |
| 2005/0046532 A1* | 3/2005 | Dodd .................. G01R 33/385 335/299 |

(Continued)

FOREIGN PATENT DOCUMENTS

| JP | 2008-543416 A | 12/2008 |
| JP | 2009-039326 A | 2/2009 |

(Continued)

OTHER PUBLICATIONS

Communication dated Sep. 27, 2019, issued by the State Intellectual Property Office of the P.R.C. in corresponding application No. 201680020711.2.

(Continued)

*Primary Examiner* — Thaddeus B Cox
(74) *Attorney, Agent, or Firm* — Sughrue Mion, PLLC

(57) ABSTRACT

A coil apparatus for use in a transcranial magnetic stimulation apparatus is provided to further increase an electric field intensity on a head surface. The coil apparatus includes a wound-wire coil disposed on or near a head surface so as to generate a current by an induced electric field through electromagnetic induction in a magnetic stimulation-target region of a brain for stimulating neurons. The wound-wire coil includes a near-head-surface conductive wire portion disposed on or near the head surface, and a far-head-surface conductive wire portion disposed farther from the head surface than the near-head-surface conductive wire portion. A distance between the near-head-surface conductive wire portion and the far-head-surface conductive wire portion is set to be changed so that an intensity of the induced electric (Continued)

field becomes larger than that of a surrounding region of the magnetic stimulation-target region.

3 Claims, 10 Drawing Sheets

Related U.S. Application Data

(60) Provisional application No. 62/154,295, filed on Apr. 29, 2015, provisional application No. 62/142,380, filed on Apr. 2, 2015.

(51) Int. Cl.
*A61N 2/00* (2006.01)
*A61F 2/04* (2013.01)
*A61B 5/00* (2006.01)

(56) References Cited

U.S. PATENT DOCUMENTS

| | | |
|---|---|---|
| 2006/0287566 A1 | 12/2006 | Zangen et al. |
| 2012/0053449 A1 | 3/2012 | Moses et al. |
| 2012/0157752 A1 | 6/2012 | Nishikawa et al. |
| 2014/0235927 A1 | 8/2014 | Zangen et al. |
| 2014/0357935 A1* | 12/2014 | Ilmoniemi ............. A61N 2/004 600/13 |
| 2015/0196772 A1 | 7/2015 | Ghiron et al. |
| 2016/0346562 A1 | 12/2016 | Saitoh et al. |

FOREIGN PATENT DOCUMENTS

| | | |
|---|---|---|
| JP | 2012-125546 A | 7/2012 |
| WO | 2006134598 A2 | 12/2006 |
| WO | 2010100643 A2 | 9/2010 |
| WO | 2010/147064 A1 | 12/2010 |
| WO | 2013166434 A1 | 11/2013 |
| WO | 2014128630 A1 | 8/2014 |
| WO | 2014128631 A1 | 8/2014 |
| WO | 2015/122506 A1 | 8/2015 |

OTHER PUBLICATIONS

International Preliminary Report on Patentability and Translation of Written Opinion dated Oct. 12, 2017 from the International Bureau in counterpart International application No. PCT/JP2016/060492.
Communication dated Dec. 7, 2018 from the European Patent Office in application No. 16773020.9.
International Search Report for PCT/JP2016/060492, dated Jun. 21, 2016.

* cited by examiner

Fig.5

| HEIGHT OF COIL L | L=21mm | L=39mm |
|---|---|---|
| MODEL M1 (d=1mm, N=20, W=59mm) | | |
| MODEL M2 (d=2mm, N=20, W=78mm) | | |
| MODEL M3 (d=1mm, N=26, W=78mm) | | |

FRONT                                                           REAR

Fig.10B

RELATIVE VALUES ($V/V_0$) OF ELECTRIC FIELD INTENSITY

| 0.931 | 0.932 | 0.926 | 0.912 | 0.892 |
|---|---|---|---|---|
| 0.972 | 0.975 | 0.971 | 0.959 | 0.940 |
| 0.997 | 1.002 | 1.000 | 0.989 | 0.972 |
| 1.005 | 1.012 | 1.012 | 1.003 | 0.987 |
| 0.995 | 1.005 | 1.007 | 1.000 | 0.986 |

Fig.10C

RELATIVE VALUES ($V/V_0$) OF ELECTRIC FIELD INTENSITY

| 0.990 | 1.000 | 1.004 | 1.005 | 0.999 |
|---|---|---|---|---|
| 0.989 | 0.998 | 1.002 | 1.001 | 0.994 |
| 0.991 | 0.998 | 1.000 | 0.999 | 0.992 |
| 0.993 | 1.000 | 1.001 | 0.999 | 0.991 |
| 0.996 | 1.003 | 1.004 | 1.000 | 0.992 | under the US 11,491,343 B2

COIL APPARATUS FOR USE IN TRANSCRANIAL MAGNETIC STIMULATION APPARATUS PROVIDED WITH WOUND-WIRE COIL DISPOSED ON OR NEAR HEAD SURFACE

CROSS-REFERENCE TO RELATED APPLICATIONS

This is a divisional of U.S. application Ser. No. 15/563,044 filed Sep. 29, 2017, now abandoned, which was a National Stage of International Application No. PCT/JP2016/060492 filed Mar. 30, 2016 which claims the benefit of U.S. Provisional Application No. 62/142,380 filed Apr. 2, 2015 and the benefit of U.S. Provisional Application No. 62/154,295 filed Apr. 29, 2015. The contents of the above-named applications are incorporated herein by reference in their entireties.

BACKGROUND

The present invention relates to a coil apparatus for use in a transcranial magnetic stimulation apparatus, a method of manufacturing the coil apparatus, a transcranial magnetic stimulation apparatus including the coil apparatus for use in the transcranial magnetic stimulation apparatus, and a method of manufacturing the transcranial magnetic stimulation apparatus.

BACKGROUND ART

Transcranial magnetic stimulation (TMS) is a painless and non-invasive treatment method of stimulating cranial nerves.

FIG. 1 is a perspective view showing an exemplary structure of a representative transcranial magnetic stimulation system of a prior art. In performing the treatment, as shown in FIG. 1, a stimulation coil is disposed so as to be in contact with the surface of the head at a proper position, and a magnetic field is caused to be instantaneously generated. Thus, the induced electric field stimulates the nerve cells in the brain positioned immediately below the coils. The magnetic field generated by the coil induces an electric field in vivo through electromagnetic induction, and this leads to causing nerves positioned in the cerebrum to be depolarized.

The transcranial magnetic stimulation has been mainly used in functional brain mapping in the motor area and the like, as means for stimulating cranial nerves non-invasively and painlessly. Further, in recent years, clinical studies clearly aiming at treatment are actively conducted on neurological disorders such as pains, Parkinson's disease, and depression, or on evaluation of the spinal cord and peripheral neuropathies. In relation to such neurological disorders, drug therapies are not very successful with some clinical cases. Accordingly, the transcranial magnetic stimulation has been gathering attention as a patient-friendly therapy, which would replace electrical stimulation treatments associated with a craniotomy procedure. As an example, it was reported that applying magnetic stimulation to the primary motor area of the cerebrum for intractable neuropathic pains relieved the patient of pain for about one day.

As shown in FIG. 1 which schematically shows an exemplary representative structure, a transcranial magnetic stimulation system 1 (hereinafter also referred to as "a magnetic stimulation system", "a transcranial magnetic stimulation apparatus", "a transcranial magnetic stimulation therapy system", or "a transcranial magnetic stimulation system") is configured to generally includes a stimulation coil 2 (magnetic field generating means), and a magnetic stimulation control apparatus 6 electrically connected to the stimulation coil 2 via a cable 4, and intended to cure and/or alleviate the symptoms of a patient M sitting on a therapeutic chair 8 by applying magnetic stimulation of a predetermined intensity to the cranial nerves through the stimulation coil 2 arranged on the scalp surface of the patient M.

In the exemplary structure of the representative system shown in FIG. 1, a coil holder 10 including the coil 2 is fixed to the tip portion of a holder fixer 11 (attitude retaining means). The holder fixer 11 is configured to include a post 11a and a base 11b, and a part of the post 11a (near the tip of the holder fixer 11) is formed by a metal-made flexible tube 11c. Accordingly, the coil 2 can be fixed to the optimum coil position just by the coil holder 10, which is shifted to a predetermined position in the scalp surface of the patient M. It is noted that the transcranial magnetic stimulation system is not limited to the structure shown in FIG. 1, and may be structured in other manner.

The stimulation coil 2 generates a dynamic magnetic field for applying magnetic stimulation to at least a particular site in the brain of the patient M. The stimulation coil 2 may be any of known various magnetic coils. In the exemplary representative structure system shown in FIG. 1, the stimulation coil 2 is a so-called figure-eight-shaped spiral coil configured to include two spiral coils arranged on an identical plane to form a figure of "eight". With the stimulation coil of this type, when a current flows through the two coils in an identical direction (for example, in the direction represented by an arrow), the maximum induced current density can be obtained immediately below the portion where the coils overlap each other. The stimulation coil (magnetic coil) 2 of this type is suitable for providing localized stimulation within the stimulation-target cerebral cortex.

Similarly, in the structure of the representative system shown in FIG. 1, the magnetic stimulation control apparatus 6 controls supply of current pulse to the stimulation coil 2. The magnetic stimulation control apparatus 6 may have any of known various structures. The user turns ON/OFF the magnetic stimulation control apparatus 6. In addition, the user can also set the intensity of current pulse, the pulse waveform and the like that determine the intensity or cycle of magnetic stimulation.

Applying accurate localized stimulation from the coil disposed on the scalp surface of the patient to the cranial nerves immediately below the coil achieves a higher pain alleviation effect. Accordingly, in medical settings, the optimum coil position and attitude of the coil 2, which minimize the neuropathic pain of the patient, are determined by using a dedicated positioning apparatus at the initial clinical examination of the patient.

However, the conventional magnetic stimulation apparatus is only available in well-equipped medical settings because it weighs about 70 kg, and requires electrical construction for installation. In addition, practical treatment requires practice of an experienced medical professional, because the stimulation position is determined with reference to MRI (Magnetic Resonance Imaging) data of the patient.

PRIOR ART DOCUMENTS

Patent Documents

[Patent Document 1] Japanese Patent Laid-open Publication No. JP2012-125546A

[Patent Document 2] International Publication No. WO2010/147064A1

[Patent Document 3] International Publication No. WO2015/122506A1

SUMMARY OF THE INVENTION

Problems to be Solved by the Invention

For transcranial magnetic stimulation therapy, various shapes of stimulation coils for magnetic stimulation methods have been currently proposed, such as a circular coil, a figure-eight-shaped coil, as well as a four-leaf coil, a Hesed coil, and a multiplicity of small circular coils arranged on a head surface. Currently, the figure-eight-shaped coil is mainly employed. The figure-eight-shaped coil consists of two series-connected circular coils, which are disposed so as to partially overlap with each other at their respective circular shape ends, for example. By allowing a current to flow through the circular coils in opposite directions, the figure-eight-shaped coil is capable of concentrating eddy currents immediately below the coil intersecting part, to provide localized stimulation.

On the other hand, stimulation to a wider range may be effective rather than the localized stimulation, depending on the target of the treatment or the symptom of an individual patient. In addition, a coil that provides localized stimulation requires accurate positioning to the target site. In this case, the accurate positioning must be carried out with a navigation system or the like.

When magnetic stimulation for use in a home treatment is under development, a navigation system for manually determining a stimulation position by a non-medical professional has been also developed. As an exemplary navigation system for determining the magnetic stimulation position, the description will be given of a positioning operation using a navigation system for a magnetic stimulation therapy coil, which detects the position and orientation of the magnetic stimulation coil as a magnetic field source in a three-dimensional space by an inverse analysis scheme using a plurality of magnetic sensors mounted in eyeglasses, and teaches a coil shifting operation so as to attain the irradiation position and orientation of the magnetic stimulation coil which are prescribed values predetermined by a medical doctor.

In a hospital, a patient firstly wears eyeglasses equipped with a plurality of magnetic sensors. Next, a medical doctor brings a magnetic stimulation coil nearer to the irradiation-target position in the cerebral cortex of the patient. The medical doctor makes trial magnetic stimulation, to determine an optimum stimulation position (the prescribed position). At the same time, the medical doctor records data table associating a plurality of pieces of data obtained at the optimum stimulation position and a plurality of surrounding positions within a range of 5 cm with each other. The data associated with each other are the position and orientation data of the magnetic stimulation coil tracked by a stereo camera, and the magnitude data of a magnetic field generated by a permanent magnet built in the coil and detected by the magnetic sensors of the eyeglasses.

In the case where the patient himself/herself practices the treatment at home moving the magnetic stimulation coil, the patient specifies the present three-dimensional position and orientation of the coil by comparing the present magnetic sensor detection value against the previously collected magnetic sensor value in the data table. The monitor screen beside the patient displays an image obtained by the magnetic stimulation coil which is overlaid on a brain MR image. Thus, observing the monitor screen, the patient can visually and instinctively recognize the present position of the magnetic stimulation coil relative to the target prescribed position, and easily shift the magnetic stimulation coil to the prescribed position so as to position the coil. It is noted that the navigation system may be structured in other manner.

It is assumed that a guidance error in the navigation system having the above-described structure is for example 5 mm at a maximum from the optimum stimulation position, and the above-described figure-eight-shaped coil can therapeutically effectively stimulate the target site if the irradiation site (the optimum stimulation position) is located within a distance of 5 mm. In this case, with a treatment apparatus that applies magnetic stimulation with the figure-eight-shaped coil at a stimulation position guided by the navigation system, the stimulation effective range of the treatment coil may fail to cover the irradiation target site (the optimum stimulation position). Hence, it is difficult to accurately stimulate the treatment target site. Accordingly, there is a need to develop a coil capable of generating eddy current evenly over a wider range, so as to be capable of therapeutically effectively stimulating the target site which is located within a distance of 10 mm, for example.

Therefore, the present inventors have already proposed a dome-type coil apparatus having an unprecedented structure and filed a patent application, for implementing a stimulation coil which is highly robust (that is, capable of generating eddy current in a wider range) (for example, See Patent Document 3).

An object of the present invention is to provide a coil apparatus for use in a transcranial magnetic stimulation apparatus capable of further increasing the electric field intensity on the head surface as compared with that of the prior art, a method of manufacturing the coil apparatus, a transcranial magnetic stimulation apparatus including the coil apparatus for use in a transcranial magnetic stimulation apparatus, and a method of manufacturing the transcranial magnetic stimulation apparatus.

Means for Dissoving the Problems

According to the present invention, there is provided a coil apparatus for use in a transcranial magnetic stimulation apparatus including a wound-wire coil disposed on or near a head surface so as to generate a current by an induced electric field through electromagnetic induction in a magnetic stimulation-target region of a brain for stimulating neurons. The wound-wire coil includes a near-head-surface conductive wire portion disposed on or near the head surface, and a far-head-surface conductive wire portion disposed farther from the head surface than the near-head-surface conductive wire portion. A distance between the near-head-surface conductive wire portion and the far-head-surface conductive wire portion is set to be changed so that an intensity of the induced electric field becomes larger than that of a surrounding region of the magnetic stimulation-target region.

Effect of the Invention

Accordingly, the present invention can further increase the electric field intensity on the head surface as compared with that of the prior art.

BRIEF DESCRIPTION OF THE DRAWINGS

FIG. 5 is a table showing implementation examples using parameters such as a height L of the dome-type coil in the transcranial magnetic stimulation apparatus shown in FIG. 2A.

FIG. 10B is a simulation result with the figure-eight-shaped coil according to the present embodiment, and shows a table showing relative values of the electric field intensity at measurement position shown in FIG. 10A.

FIG. 10C is a simulation result with the dome-type coil according to the present embodiment, and shows a table showing relative values of the electric field intensity at the measurement position shown in FIG. 10A.

MODE FOR CARRYING OUT THE INVENTION

Figure 1:
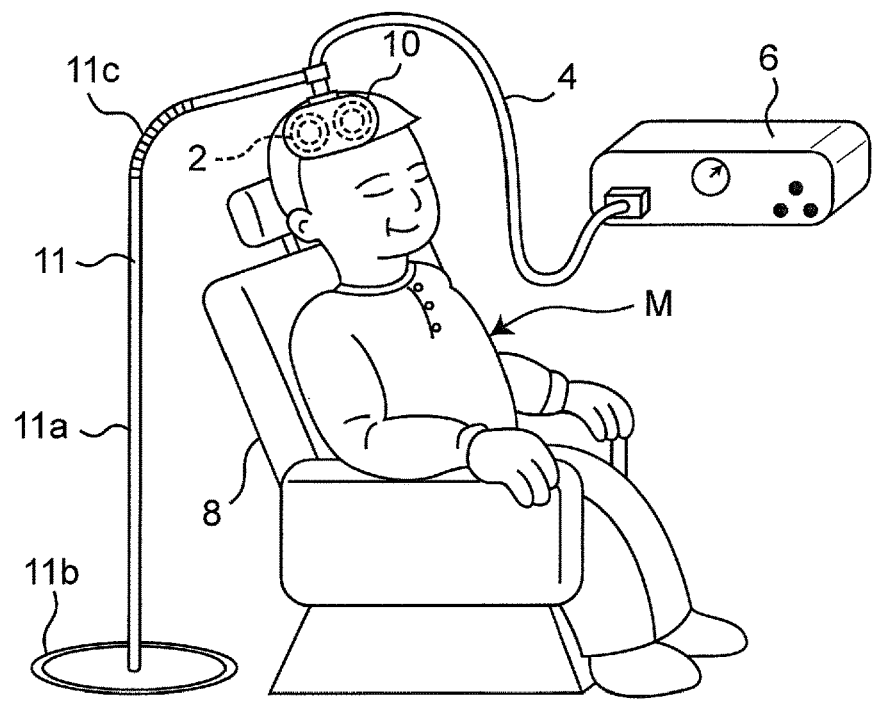
FIG. 1 is a perspective view showing an exemplary structure of a representative transcranial magnetic stimulation system according to a prior art.

Hereinafter, with reference to the drawings, a description will be given of a coil apparatus for use in a transcranial magnetic stimulation apparatus, a method of manufacturing the coil apparatus for use in a transcranial magnetic stimulation apparatus, and a transcranial magnetic stimulation apparatus according to an embodiment of the present invention. It is noted that in the following embodiment, similar constituents are denoted by an identical reference character.

Configuration of Magnetic Stimulation Coil Drive Circuit

In order to apply current to a magnetic stimulation coil (hereinafter also referred to as "a treatment coil", "a stimulation coil", or simply "a coil") so as to generate an electric field for the magnetic stimulation therapy, a transcranial magnetic stimulation system 1 includes a magnetic stimulation control apparatus 6 connected to a stimulation coil 2, and the magnetic stimulation control apparatus 6 includes a coil drive circuit within the magnetic stimulation control apparatus 6.

Figure 2A:
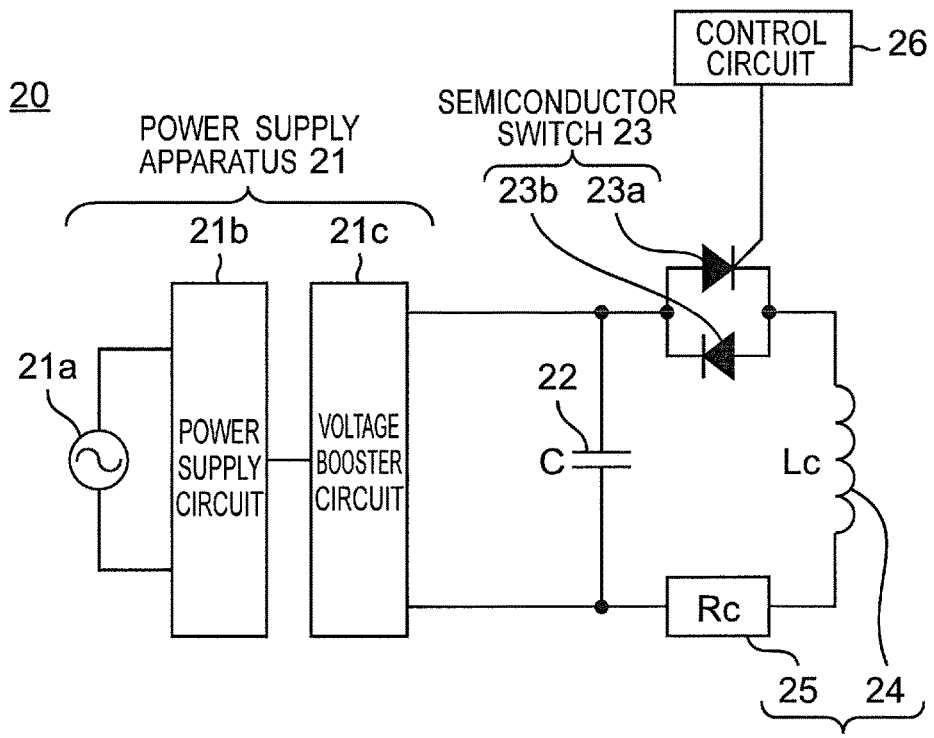
FIG. 2A is a circuit diagram showing an exemplary configuration of a stimulation coil drive circuit of a transcranial magnetic stimulation apparatus according to one embodiment of the present invention.
Figure 2B:
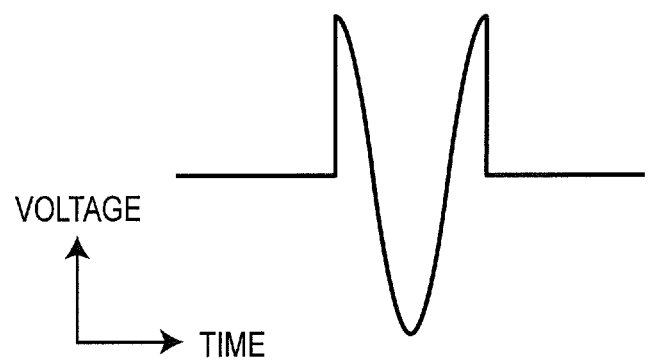
FIG. 2B is a waveform diagram showing a coil voltage waveform of the transcranial magnetic stimulation apparatus shown in FIG. 2A.
Figure 2C:
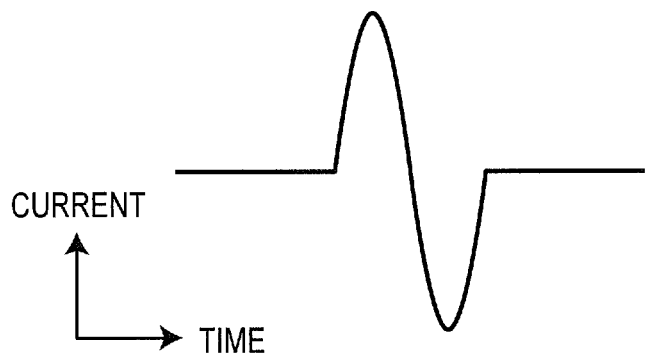
FIG. 2C is a waveform diagram showing a coil current waveform of the transcranial magnetic stimulation apparatus shown in FIG. 2A.

FIG. 2A is a circuit diagram showing an exemplary configuration of the stimulation coil drive circuit of the transcranial magnetic stimulation apparatus according to one embodiment of the present invention. FIG. 2B is a waveform diagram showing a coil voltage waveform of the transcranial magnetic stimulation apparatus shown in FIG. 2A. FIG. 2C is a waveform diagram showing a coil current waveform of the transcranial magnetic stimulation apparatus shown in FIG. 2A.

The coil drive circuit 20 includes a power supply apparatus 21, a capacitor 22, a semiconductor switch 23, the stimulation coil 2, and a control circuit 26. In this case, the power supply apparatus 21 includes an AC power supply 21a, a power supply circuit 21b, and a voltage booster circuit 21c. In this case, the semiconductor switch 23 is configured to include a thyristor 23a and a diode 23b reversely connected in parallel to the thyristor 23a. The thyristor 23a is turned ON/OFF based on a control signal from the control circuit 26. In addition, the capacitor 22 having capacitance C, the semiconductor switch 23, an inductance component 24 of the stimulation coil 2 having inductance Lc, and a resistance component 25 of the stimulation coil 2 having resistance value Rc are connected in series.

In the coil drive circuit 20 shown in FIG. 2A, after the power supply apparatus 21 accumulates electric charges in the capacitor 22, by the thyristor 23a turned ON (energized), a resonance occurs between the capacitor 22 and the inductance component 24 of the stimulation coil 2. In this case, when neglecting the resistance component 25, the current "i" flowing in the inductance component 24 during the resonance is represented by the following differential equation:

$$Lc\frac{d^2 i}{dt^2} + \frac{i}{C} = 0 \tag{1}$$

Accordingly, the current "i" is represented by the following equation using boosted voltage $V_0$:

$$i = V_0 \sqrt{\frac{C}{Lc}} \sin\frac{t}{\sqrt{LcC}} \tag{2}$$

As can be seen from Equations (1) and (2), when the thyristor 23a is turned OFF (disconnected) after a lapse of time corresponding to one resonance cycle, the waveform of coil voltage (the voltage across the terminals of the inductance component 24 of the stimulation coil 2) and the waveform of the current flowing through the stimulation coil 2 are shown in FIG. 2B and FIG. 2C, respectively. It is noted that, in FIG. 2B, the horizontal axis represents the time, and the vertical axis represents the voltage. In FIG. 2C, the horizontal axis represents the time and the vertical axis represents the current.

In a representative transcranial magnetic stimulation system, the voltage applied to the stimulation coil 2 is 0.4 kV to 3 kV, and the current flowing through the stimulation coil 2 is 4 kA to 20 kA. In addition, it is said that the pulse width suitable for the transcranial magnetic stimulation therapy is 200 μs to 300 μs, and the intensity of an induced electric field that is generated in the brain is about 200 V/m when the conductivity of the gray matter is 0.1 S/m. In this case, the stimulation intensity and the reactive effect obtained by the stimulation intensity may change depending on subjects, and often are of an empirical nature.

Next, a description will be given of the structure of a dome-type coil apparatus which is the basis of the study conducted by the present inventors on the coil apparatus according to the present embodiment.

Figure 3:
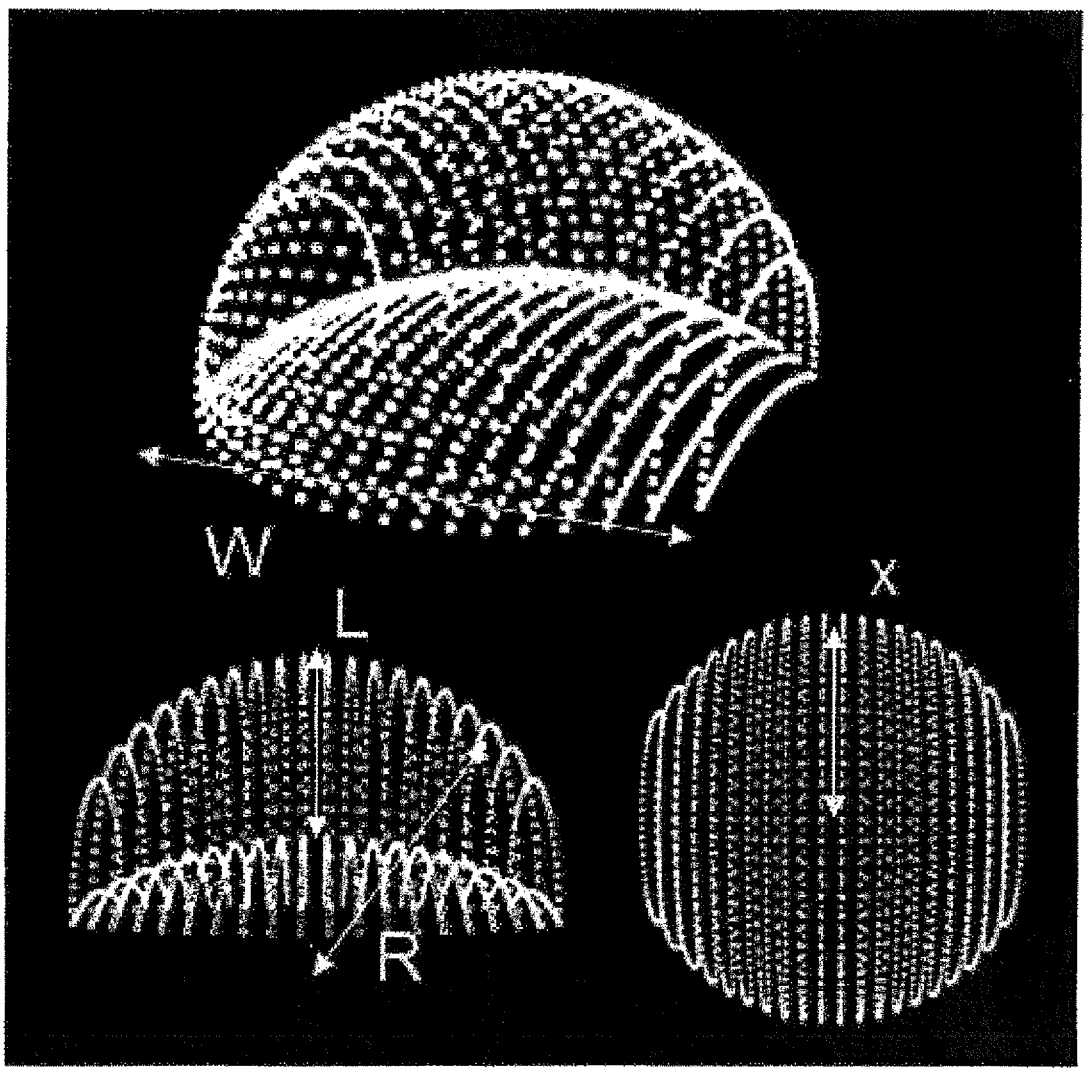
FIG. 3 is a schematic appearance diagram of a dome-type coil used in the present embodiment.

FIG. 3 is a schematic appearance diagram of a dome-type coil used in the present embodiment. A patent application was filed for the dome-type coil for achieving wider-area stimulation than that of the conventional figure-eight-shaped coil (for example, See Patent Document 3). The dome-type coil primarily has independent parameters, namely, a number of turns "N", a height "L", and a conductor wire interval "d", and further has parameters which are dependent on the independent parameters, namely, a coil width W and an upper hemisphere radius R. Hereinafter, these parameters are also collectively referred to as "variable parameters".

In addition, the implementation example according to Patent Document 3 has constant parameters, namely, a radius of a lower in-contact surface of the sphere r=100 mm, and a cross section of a rectangular copper wire=2 mm×6 mm. Further, a radius of an in-contact portion of a bottom surface x, in a top view of the coil (See FIG. 3) is defined as an auxiliary parameter. As can be seen from these definitions, when the coil is designed with reference to the in-contact portion of the bottom surface, the values of radius x and height L uniquely determine the radius R.

It is noted that the dome-type coil according to the present embodiment can be also defined as follows. That is, the dome-type coil according to the present embodiment is a coil apparatus that includes a near-head-surface conductive wire portion disposed near a head surface, and a far-head-surface conductive wire portion disposed distant from the head surface. The near-head-surface conductive wire portion and the far-head-surface conductive wire portion are electrically connected to each other to form one turn of a coil. A plurality of the turns of the coil are arranged having their respective centers continuously juxtaposed to each other, and the shape of the near-head-surface conductive wire portion and/or the far-head-surface conductive wire portion is identical between adjacent ones of the turns or gradually different between adjacent ones of the turns.

Alternatively, the dome-type coil according to the present embodiment is a coil apparatus for use in the transcranial magnetic stimulation therapy where the coil apparatus includes a wound-wire coil. In this case, the wound-wire coil is disposed on or near a head surface so that center axes of turns of the wound-wire coil become substantially parallel to the head surface, and the electromagnetic induction generates a current in the brain to stimulate neurons.

With the dome-type coil under the foregoing definition, the coil height L can be defined as the maximum value of the distance between the near-head-surface conductive wire portion and the far-head-surface conductive wire portion in each of the turns of the coil structuring the dome-type coil.

While the above-described embodiment discusses the dome-type coil, the present invention is not limited thereto, and the present invention may be a figure-eight-shaped coil that includes a coil being the near-head-surface conductive wire portion and a coil being the far-head-surface conductive wire portion. In this case, the figure-eight-shaped coil is a coil apparatus for use in a transcranial magnetic stimulation apparatus, where the coil apparatus includes a wound-wire coil disposed on or near a head surface so that center axes of the turns of the wound-wire coil become substantially perpendicular to the head surface, and this leads to that electromagnetic induction generates a current in the brain to stimulate neurons.

Policies of Study Conducted by Present Inventors

On the basis of the dome-type coil having the above-described parameters, the present inventors conducted the study leading to the coil apparatus according to the present embodiment based on the following course and knowledge.

First of all, upon designing the coil apparatus for use in a transcranial magnetic stimulation apparatus, the stimulation to a magnetic stimulation treatment target area on the brain surface, for example to the sensory area adjacent to the primary motor area, is safe. On the other hand, the stimulation to the memory area such as the hippocampus must be avoided. Accordingly, upon designing the coil apparatus, the present inventors set a stimulation range of about 1.5 times vertically and horizontally as great as the stimulation range of the conventional figure-eight-shaped coil.

In addition, any reduction in the stimulation efficiency would necessitate application of a greater amount of current to the coil, which would cause the coil to generate heat and consequently interfere with continuous stimulation. Thus, upon designing, the present inventors have placed importance also on preventing any reduction in the stimulation efficiency.

The patent application previously filed by the present inventors proposes a novel dome-type coil capable of evenly stimulating a wider range than that of a figure-eight-shaped coil, and discusses the influence on the induced electric field when the height L, the coil width W, and the upper hemisphere radius R are independently changed.

However, the inventors found out that the relationship between these design parameters and the spread or intensity of the resultant induced electric field that was generated on the head was complicated, and the optimum designing of the dome-type coil was hardly achieved by the designing approach involving independently changing these parameters.

In the present embodiment, as will be described in detail later, the present inventors newly adopted an approach upon designing the dome-type coil, using "the area of the bottom surface of the coil being in contact with the head" as the fixed reference. As a result, the present inventors found out that "the spread" and "the intensity" of the resultant induced electric field depended on "the area being in contact with the head" and "the coil height and the density of turns", respectively. This finding made it possible to change the intensity of the resultant induced electric field with maintaining the spread of the electric field to be constant, and hence facilitated the designing of the dome-type coil in term of searching for an optimum value. Hereinafter, a description will be given specifically of the result of the study based on such a course conducted by the present inventors.

Method of Calculating Induced Electric Field for Head Model Using Scalar-Potential Finite-Difference Method In the studies that led to the present embodiment involving calculation of an induced electric field in the transcranial magnetic stimulation in their process, the present inventors used the scalar-potential finite-difference method (SPFD method) in their studies. According to the SPFD method, a subject where an induced electric field is to be generated by a dynamic magnetic field is divided into micro rectangular parallelepipeds, and an induced electric field that is generated in each micro volume is obtained as a solution to a difference equation of the magnetic vector potential. First of all, an electric field E generated by the coil is represented as follows, using a magnetic vector potential $A_0$ and a scalar potential $\nabla \varphi$:

$$E = -\frac{\partial A_0}{\partial t} - \nabla \phi \quad (3)$$

In addition, the following equation is established by the current continuity equation and the Ohm's law for a density of induced current J, the electric field E, and a conductivity σ:

$$\nabla J = \nabla \sigma E = 0 \quad (4)$$

By the foregoing Equations (3) and (4), the following equation is established:

$$-\nabla(\nabla \sigma \phi) = \nabla\left(\sigma \frac{\partial A_0}{\partial t}\right) \quad (5)$$

Figure 4:
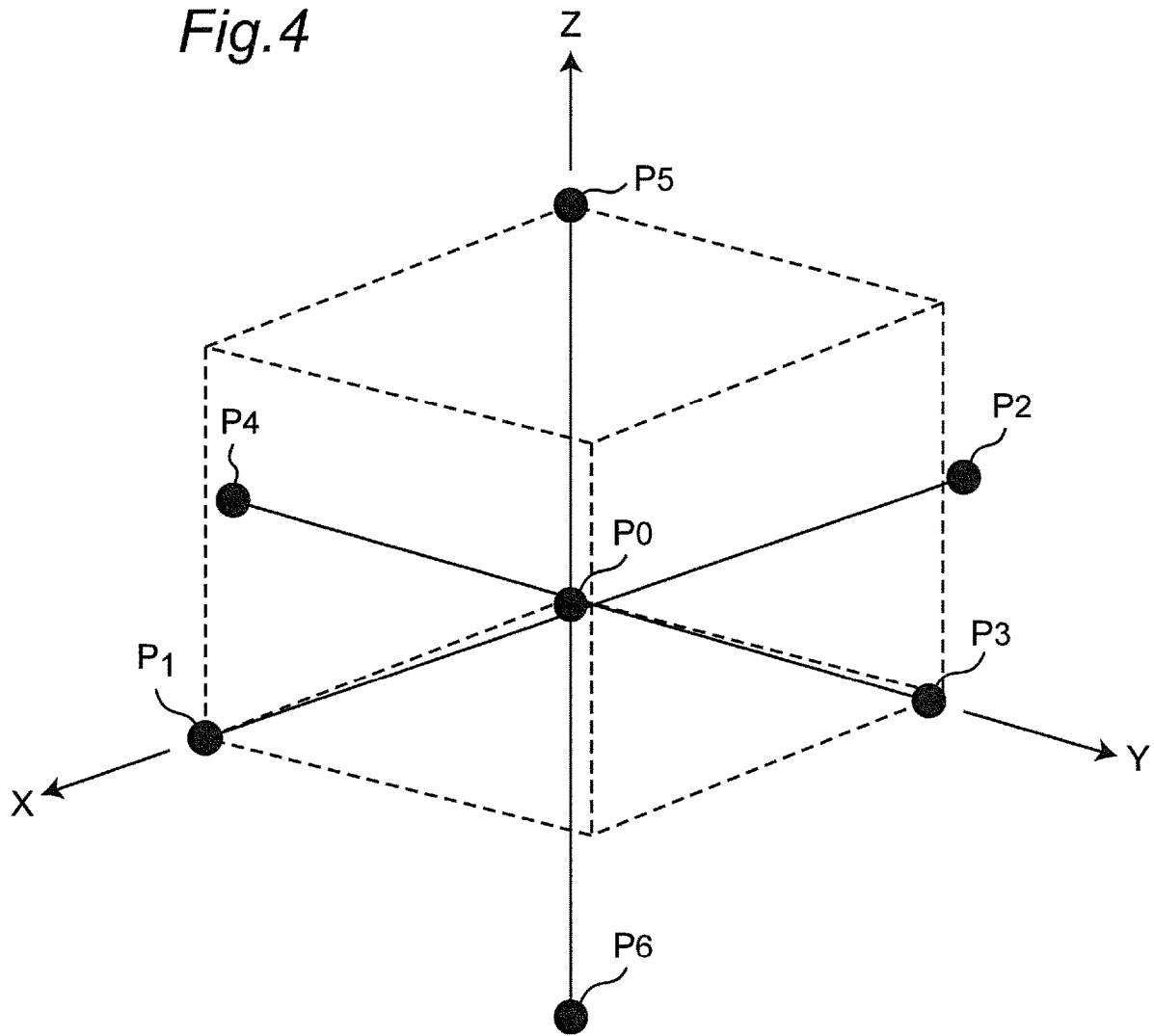
FIG. 4 is a perspective view showing a structure of a micro hexahedron for describing the principle of the scalar-potential finite-difference method used in the present embodiment.

FIG. 4 is a perspective view showing a structure of a micro hexahedron for describing the principle of the scalar-potential finite-difference method used in the present embodiment. In a virtual micro hexahedron shown in FIG. 4, Sn is a conductance of each of the lines, ln, is the length of each of the lines, Φn is a scalar potential at a node Pn, and $A_0$n is a magnetic vector potential of the component in the direction of the line connecting between a node P0 and the node Pn. In this case, by discretizing Equations (3), (4), and (5), the following equation is established for these values:

$$\sum_{n=1}^{6} S_n \phi_n - \left(\sum_{n=1}^{6} S_n\right)\phi_0 = \sum_{n=1}^{6} (-1)^n S_n l_n \frac{\partial A_{0n}}{\partial t} \quad (6)$$

By solving the equation for the entire voxels, an induced electric field E (vector) is obtained.

Implementation Example 1

Changes in Induced Electric Field with Area of in-Contact-with-Head Portion of Dome-Type Coil being Constant and Height and Conductive Wire Density being Changed FIG. 5 is a table showing implementation examples of the transcranial magnetic stimulation apparatus shown in FIG. 2A with adopting parameters such as the height L of the dome-type coil and the like. In order to analyze changes in the stimulation effect for the parameters, as shown in FIG. 5, the present inventors firstly provided a plurality of coil models with the coil heights L of 21 mm and 39 mm, and the area of the surface in contact with the head that is calculated based on x=56 mm, which are fixed values based on the design value, and analyzed changes in the induced electric field in each hemispheric conductor simulating a head. It is noted that the dome-type coil is configured to include a plurality of turns with their respective elements connected in series, for example. The width between respective elements of two adjacent turns is defined as an element width d.

In this case, since the height L was changed when the area in contact with the dead (in-contact-with-head area) was maintained to be constant, the radius (R in FIG. 3) of the upper-side conductive wire of the dome-type coil changed from 60.2 mm to 56 mm in accordance with the height L. The following three types of coil models having other different parameters were provided.

(Model M1) the number of turns N=20, the element width d=1 mm, and the coil width W=59 mm;
(Model M2) the number of turns N=20, the element width d=2 mm, and the coil width W=78 mm; and
(Model M3) the number of turns N=26, the element width d=1 mm, and the coil width W=78 mm.

It is noted that comparison between Model M2 and Model M3 shows changes in the induced electric field when the conductive wire density is changed with the in-contact area maintained. In addition, based on that the coil height L is changed to be 21 mm and 39 mm, Model M1 is referred to as Model group M1, Model M2 is referred to as Model group M2, and Model M3 is referred to as Model group M3.

The conductor where an induced electric field is to be generated has a shape of hemisphere having a radius of 75 mm, and a conductivity σ=0.1 S/m, and is set at a position 10 mm below the coil model. The current of 5.3 kA with 4 kHz was applied to the stimulation coil. Then, as described below, changes in the intensity and spread of the induced electric field for the variations in the coil height L were calculated based on the scalar-potential finite-difference method and their calculated data is compared with each other.

Figure 6:
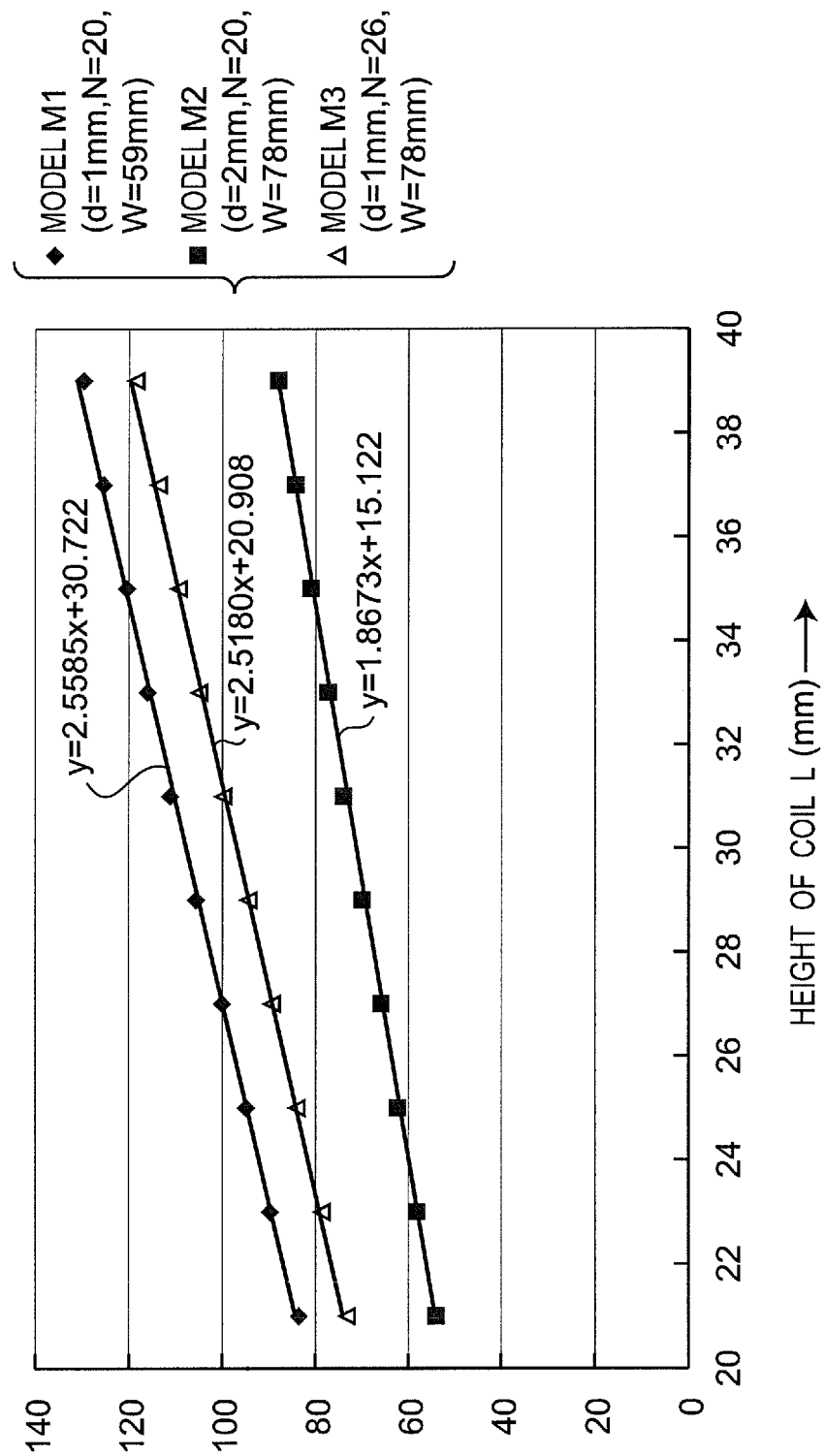
FIG. 6 is a graph showing an intensity of an electric field that the dome-type coil generates when the height L of the dome-type coil is changed in the transcranial magnetic stimulation apparatus shown in FIG. 2A.

FIG. 6 is a graph showing an intensity of the electric field that the coil generates when the height L of the dome-type coil is changed in the transcranial magnetic stimulation apparatus shown in FIG. 2A. As shown in FIG. 6, it was found out that the stimulation range did not change for variations in the height L of the dome-type coil, and just the intensity is proportional to the height L. That is, Model group M1 where N=20 and the element width d=1 mm showed an average intra-sphere value of 83 V/m to 129 V/m in an induced electric field having a radius of 10 mm at the stimulation point center, and Model group M2 where N=20 and the element width of 2 mm showed an average intra-sphere value of 54 V/m to 87 V/m in such a field. Thus, the intensity of the induced electric field became larger as the coil height was higher.

In this case, "the average intra-sphere value of the induced electric field" refers to the value obtained by calculating an electric field intensity for each of points in the sphere covering a predetermined radius from a center point; and calculating the average value thereof. In addition, Model group M3 where the area of the in-contact portion was not changed and the conductive wire density was changed showed the average intra-sphere value of the induced electric field of 73 V/m to 118 V/m, that is, just the intensity increased while the spread of the induced electric field showed no change as compared with that of Model group M2. It is noted that the spread of the induced electric field is the value that is defined with reference to a point where the generated induced electric field attenuates by 50% as great as the maximum value. The half width of the Model group M1 was 8.7 cm×4.2 cm and the half width of Model groups M2 and M3 was 9.7 cm×5.3 cm.

These results showed that, upon designing the dome-type coil, increasing both of the coil height L and the winding density with no change in the area of the in-contact portion maximizes the intensity without increasing or reducing the spread of the generated induced electric field. This is an important finding for aiming at designing a coil which is capable of achieving efficient stimulation without involving an unnecessary increase in the induced electric field.

However, since a larger coil height L or a larger winding density increases the flux linkage for the coil body, self-inductance Lc of the coil increases. In this case, the pulse width T of the current that the above-described general drive circuit generates is determined as follows by using a self-inductance Lc of the coil and a capacitance C of the circuit:

$$T=2\pi\sqrt{LcC} \tag{7}$$

In general, the pulse width of the current applied to the stimulation coil capable of efficiently stimulating nerves is said to be 200 μs to 300 μs. Then, accordingly, in the case of a capacitance C=180 μF, the limit value of the inductance is about 13 μH. By calculating the inductance for each coil model in view of the foregoing, in the case of the coil height L=39 mm with Model group M2 where the spread of the induced electric field is sufficient, the inductance can be calculated as 9.0 μH. This value is sufficiently low based on the reference value 13 μH, and a margin is still provided in view of a pulse width effective in terms of treatment.

Based on the foregoing, obtaining an inductance value with a raised coil height L provides 12.9 μH in the case of L=49 mm, which is the optimum coil height that does not provide any inductance value exceeding the reference 13 μH. In this case, the coil intensity as an extrapolation value calculated by an approximated straight line obtained from the result was 107 V/m, and the coil intensity as a result of analyzing the induced electric field from the foregoing equations under the same experimental result was 103 V/m.

It is noted that, in the case of C=180 μF with a pulse width of the current applied to the stimulation coil of 200 μs, the minimum value of the inductance is 5.63 μh, and the inductance should be preferably at least 5 μH or larger.

Implementation Example 2

Comparison in Induced Electric Field for Hemispheric Model Between Figure-Eight-Shaped Coil and Dome-Type Coil Next, in order to evaluate the robustness of the dome-type coil in terms of position, the spread and intensity of an induced electric field for the hemispheric model was compared between the figure-eight-shaped coil and the dome-type coil.

Figure 7A:
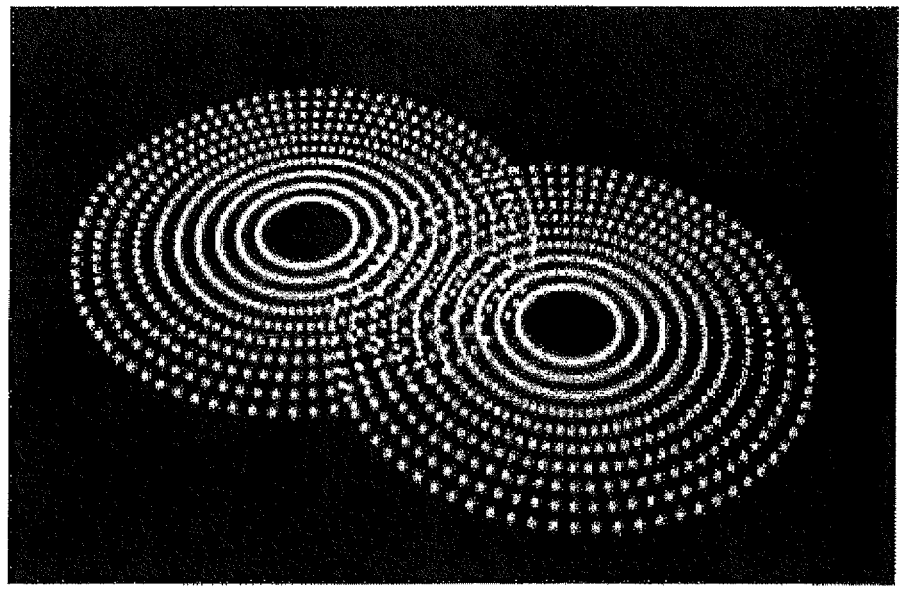
FIG. 7A is a perspective view showing a schematic appearance of the figure-eight-shaped coil used in the present embodiment.
Figure 7B:
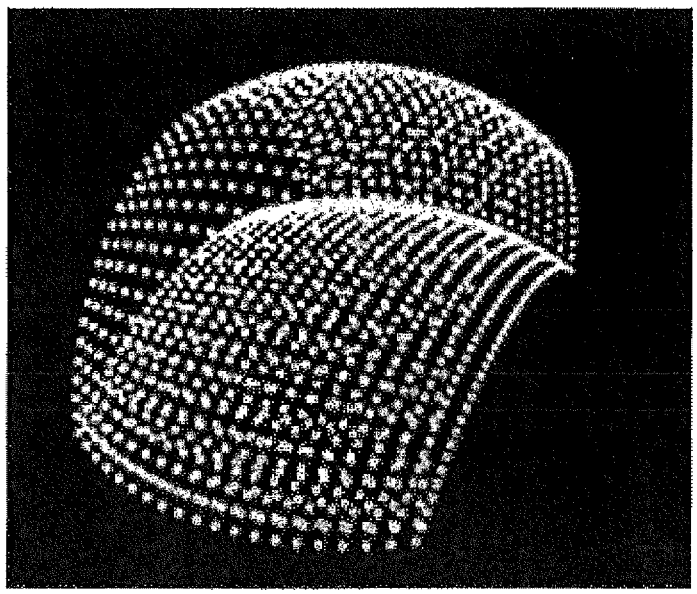
FIG. 7B is a perspective view showing a schematic appearance of the dome-type coil used in the present embodiment.

FIG. 7A is a perspective view showing a schematic appearance of the figure-eight-shaped coil used in the present embodiment. FIG. 7B is a perspective view showing a schematic appearance of the dome-type coil used in the present embodiment.

As shown in FIG. 7A, the figure-eight-shaped coil is configured to include two circular coils overlapped on each other, where each of the circular coils has an outer radius of 51 mm, an inner radius of 11 mm, and 10 turns. The dome-type coil has values of N=20, d=2, W=78 mm, L=39 mm, and R=66 mm. The hemispheric model is similar to that used in the above-described study. The current flowing through the coils is 5.3 kA with 3.4 kHz.

As to the induced electric field that is generated at the hemispheric model, the spread range of the dome-type coil where the stimulation intensity attenuates by half was 9.8 cm×5.4 cm, and that of the figure-eight-shaped coil was 6.0 cm×3.4 cm. In addition, the average value of the induced electric field that is generated within a sphere of a radius of 10 mm about the top of the hemisphere was 83 V/m with the dome-type coil and 169 V/m with the figure-eight-shaped coil. The result thereof is shown in Table 1.

TABLE 1

|  | Figure-eight-shaped coil | Dome-type coil |
| --- | --- | --- |
| Electric field intensity (average value in 10 mm sphere) | 169 V/m | 83 V/m |
| Spread (50% attenuation width) | 6.0 cm × 3.4 cm | 9.8 cm × 5.4 cm |

Figure 8A:
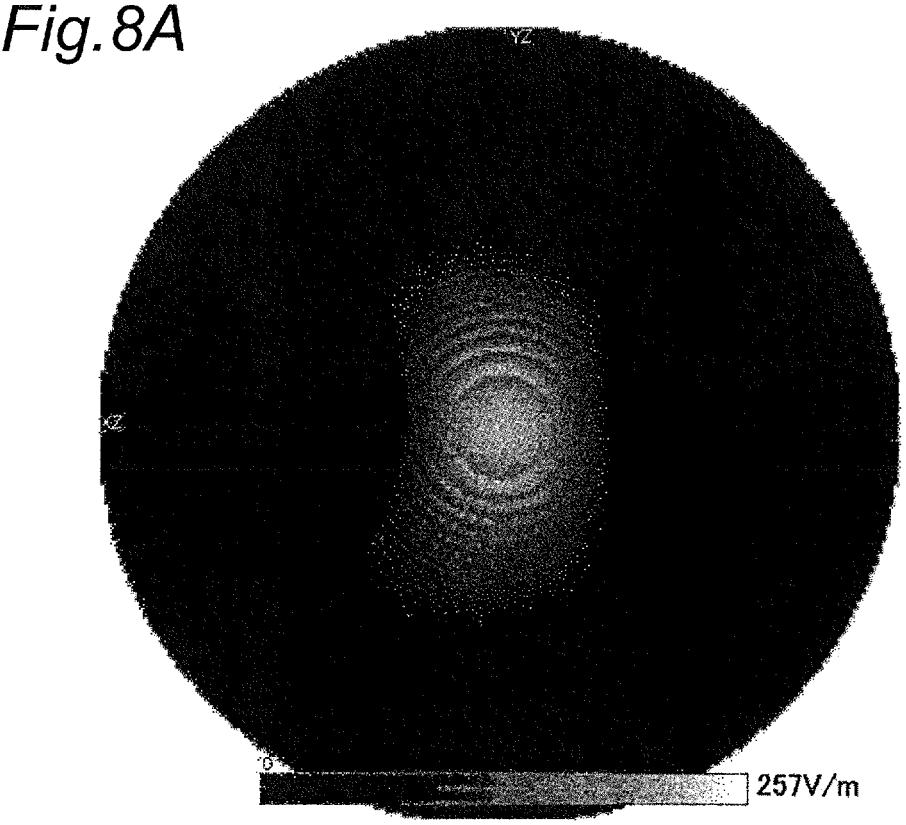
FIG. 8A is a simulation result with the figure-eight-shaped coil according to the present embodiment, and shows an image showing an intensity of an induced electric field that is generated on a hemispheric model surface.
Figure 8B:
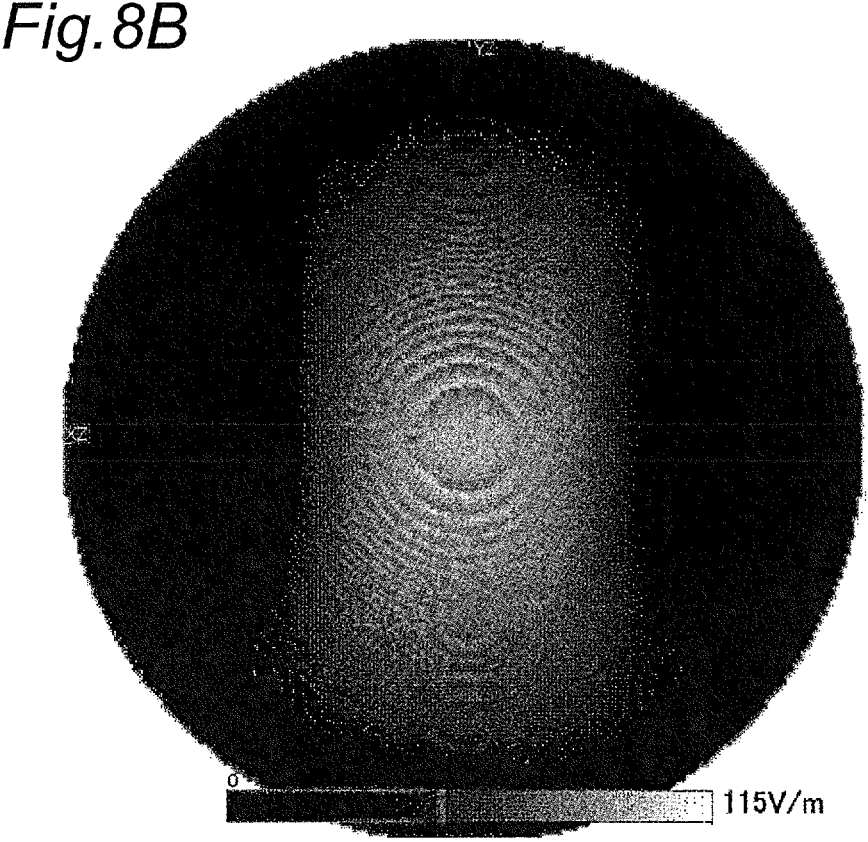
FIG. 8B is a simulation result with the dome-type coil according to the present embodiment, and shows an image showing an intensity of an induced electric field that is generated on the hemispheric model surface.
Figure 9A:
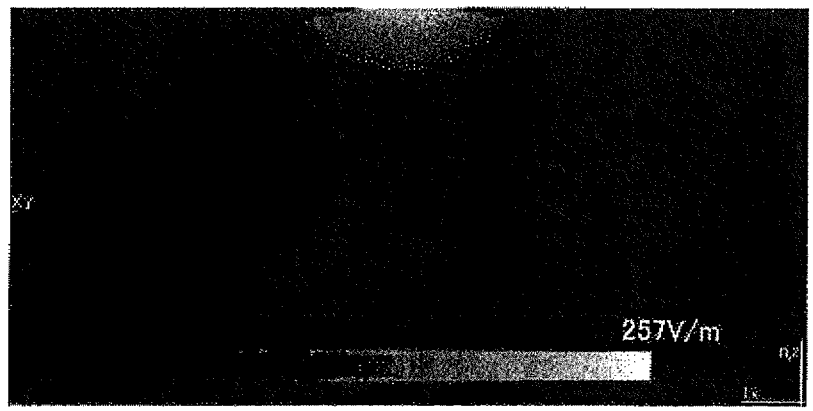
FIG. 9A is a simulation result with the figure-eight-shaped coil according to the present embodiment, and shows an image showing an intensity of an induced electric field that is generated on a hemispheric model section surface.
Figure 9B:
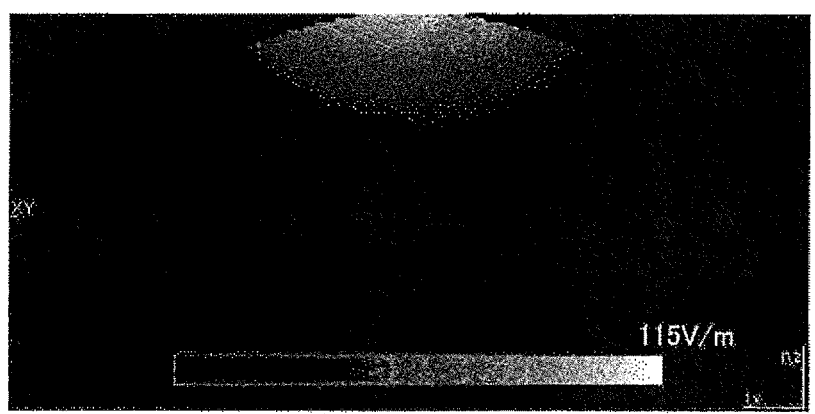
FIG. 9B is a simulation result with the dome-type coil according to the present embodiment, and shows an image showing an intensity of an induced electric field that is generated on the hemispheric model section surface.

FIG. 8A is a simulation result with the figure-eight-shaped coil according to the present embodiment, and shows an image showing an intensity of an induced electric field that is generated on the hemispheric model surface. FIG. 8B is a simulation result with the dome-type coil according to the present embodiment, and shows an image showing an intensity of an induced electric field that is generated on the hemispheric model surface. FIG. 9A is a simulation result with the figure-eight-shaped coil according to the present embodiment, and shows an image showing an intensity of an induced electric field that is generated on the hemispheric model section surface. FIG. 9B is a simulation result with the dome-type coil according to the present embodiment, and shows an image showing an intensity of the induced electric field that is generated on the hemispheric model section surface. That is, FIGS. 8A and 8B show the appearance of the induced electric field that is generated on the hemispheric model at the surface of the model, and FIGS. 9A and 9B show the appearance of that at the section thereof.

While the dome-type coil is inferior in stimulation intensity to the figure-eight-shaped coil, it can be seen that the dome-type coil attains a wider stimulation range for the hemispheric model. The depth of stimulation is also sufficient, which can be seen from the distance to the position where the maximum induced electric field attenuates by 50% is 9.8 mm with the figure-eight-shaped coil and 15 mm with the dome-type coil. In general, taking into consideration that misalignment in the stimulation position tolerated with the figure-eight-shaped coil is said to be about 5 mm, from the foregoing result, misalignment in the stimulation position permissible with the dome-type coil is expected to increase by about 1.5 times, i.e., about 8 mm. Thus, it can be recognized that the coil that exhibits great tolerance to misalignment is implemented.

Implementation Example 3

Evaluation Calculation of Robustness in Terms of Position of Dome-Type Coil for Brain-Shape Data Obtained by MR Image The present inventors have conducted a study based on the simulation of misalignment in a stimulation position with a 3 mm grid with 5 points×5 points about the motor area stimulation point for a brain-shape model formed by an MR image of a hemispheric subject's head.

The brain-shape model was extracted from the MR image separately for three elements, namely, the white matter, the gray matter, and the cerebrospinal fluid of the brain, by using the statistical image analysis package SPM that operates on MATLAB. The conductivity of the white matter, the gray matter, and the cerebrospinal fluid was set to 0.07 S/m, 0.11 S/m, and 1.79 S/m, respectively. The induced electric field at the originally-intended-stimulation point upon occurrence of misalignment was compared between the figure-eight-shaped coil and the dome-type coil designed in a manner similar to that of the implementation example 2.

Figure 10A:
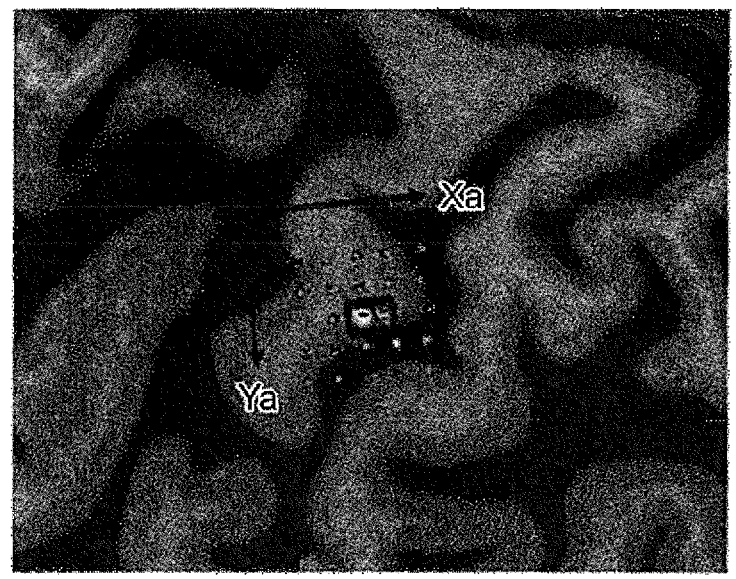
FIG. 10A is a photograph image showing a measurement position of the intensity of an electric field in an MR image of the subject's head in a simulation with the figure-eight-shaped coil and the dome-type coil according to the present embodiment.

FIG. 10A is a photograph image showing a measurement position of the intensity of an electric field in an MR image of the subject's head in the simulation with the figure-eight-shaped coil and the dome-type coil according to the present embodiment. FIG. 10B is a simulation result with the figure-eight-shaped coil according to the present embodiment, and shows a table showing relative values of the electric field intensity at the measurement position shown in FIG. 10A. FIG. 10C is a simulation result with the dome-type coil according to the present embodiment, and shows a table showing relative values of the electric field intensity at the measurement position shown in FIG. 10A. In this case, the measurement position in FIG. 10A is coordinates defined by a coordinate in Xa axis and a coordinate in Ya axis which are orthogonal to each other.

That is, FIG. 10A shows the brain shape obtained by MRI, and the appearance of the stimulation point in the primary motor area on the MR image. As a result of simulating the induced electric field attributed to stimulation, the intensity of the induced electric field was 264 V/m with the figure-eight-shaped coil and 101 V/m with the dome-type coil, each of which was obtained as the average value of the induced electric field that is generated within a sphere of a radius of 10 mm about the stimulation center point. As to attenuation of the electric field intensity upon misalignment, as shown in FIG. 10B, a stimulation point with the maximum of 10.8% reduction was observed with the figure-eight-shaped coil. This observation agrees with the report that, in some cases, the treatment effect was not exhibited due to misalignment of the coil of 5 mm or larger.

On the other hand, as shown in FIG. 10C, even at the point with the maximum reduction, just a 1.1% reduction was observed with the dome-type coil. Hence, it can be said that the dome-type coil has the design that withstands misalignment, upon performing stimulation to an actual brain complicated in shape. Further, this conclusion also agrees with the study that the stimulation position displacement tolerated with the hemispheric model was about 8 mm.

Summarizing the embodiment described above, by setting the distance between the near-head-surface conductive wire portion and the far-head-surface conductive wire portion to be changed so that the intensity of the induced electric field of the magnetic stimulation-target region increases, preferably becomes substantially the maximum, as compared to that of the surrounding region of the magnetic stimulation-target region (the region that should undergo magnetic stimulation) in the brain, the intensity of the induced electric field becomes remarkably larger than that of the prior art. In this case, it is preferable to set the distance so that the inductance Lc falls within an inductance range from 5 μH to 13 μH inclusive, and the induced electric field falls within the predetermined spread on the head surface. In addition, with the transcranial magnetic stimulation apparatus, it is preferable to set the pulse width to fall within a predetermined pulse width range, and set the distance between the near-head-surface conductive wire portion and the far-head-surface conductive wire portion to be changed so that the intensity of the induced electric field becomes remarkably larger than that of the surrounding region of the magnetic stimulation-target region.

Modified Embodiment

In the foregoing embodiment, a description has been given of the figure-eight-shaped coil configured to include two circular coils, however, the present invention is not limited thereto. The present invention may be implemented by an eccentric figure-eight-shaped coil configured to include two circular coils having their respective center axes biased toward the center of the coil apparatus. In addition, the description is given of the method of manufacturing a coil apparatus mainly focusing on the dome-type coil, however, the present invention is not limited thereto and is applicable also to a figure-eight-shaped coil or an eccentric figure-eight-shaped coil.

Summary of the Embodiments

According to the first aspect of the present invention, there is provided a coil apparatus for use in a transcranial magnetic stimulation apparatus including a wound-wire coil disposed on or near a head surface so as to generate a current by an induced electric field through electromagnetic induction in a magnetic stimulation-target region of a brain for stimulating neurons. The wound-wire coil includes a near-head-surface conductive wire portion disposed on or near the head surface, and a far-head-surface conductive wire portion disposed farther from the head surface than the near-head-surface conductive wire portion. A distance between the near-head-surface conductive wire portion and the far-head-surface conductive wire portion is set to be changed so that an intensity of the induced electric field becomes larger than that of a surrounding region of the magnetic stimulation-target region.

According to the coil apparatus for use in the transcranial magnetic stimulation apparatus of the second aspect of the present invention, in the coil apparatus for use in the transcranial magnetic stimulation apparatus of the first aspect of the present invention, the distance between the near-head-surface conductive wire portion and the far-head-surface conductive wire portion is set to be changed so that inductance of the coil apparatus falls within a predetermined inductance range and the induced electric field falls within a predetermined spread on the head surface.

According to the coil apparatus for use in the transcranial magnetic stimulation apparatus of the third aspect of the present invention, in the coil apparatus for use in the transcranial magnetic stimulation apparatus of the second aspect of the present invention, the inductance range is set to be equal to or larger than 5 μH and equal to smaller than 13 μH.

According to the coil apparatus for use in the transcranial magnetic stimulation apparatus of the fourth aspect of the present invention, in the coil apparatus for use in the transcranial magnetic stimulation apparatus of any one of the first to third aspects of the present invention, the coil apparatus is one of a dome-type coil, a figure-eight-shaped coil, and an eccentric figure-eight-shaped coil.

According to the fifth aspect of the present invention, there is provided a transcranial magnetic stimulation apparatus including the coil apparatus for use in the transcranial magnetic stimulation apparatus of any one of the first to fourth aspects of the present invention, and a drive circuit that outputs a current pulse having a predetermined pulse width to the coil apparatus. The pulse width is set to fall within a predetermined pulse width range, and a distance between the near-head-surface conductive wire portion and the far-head-surface conductive wire portion is set to be changed so that an intensity of the induced electric field becomes larger than that of a surrounding region of the magnetic stimulation-target region.

According to the transcranial magnetic stimulation apparatus of the sixth aspect of the present invention, in the transcranial magnetic stimulation apparatus of the fifth aspect of the present invention, the pulse width range is set to be equal to or larger than 200 μs and be equal to or smaller than 300 μs.

According to the seventh aspect of the present invention, there is provided a method of manufacturing a coil apparatus for use in a transcranial magnetic stimulation apparatus including a wound-wire coil disposed on or near a head surface so as to generate a current by an induced electric field through electromagnetic induction in a magnetic stimulation-target region of a brain for stimulating neurons. The wound-wire coil includes a near-head-surface conductive wire portion disposed on or near the head surface and a far-head-surface conductive wire portion disposed farther from the head surface than the near-head-surface conductive wire portion. The method includes the step of: setting a distance between the near-head-surface conductive wire portion and the far-head-surface conductive wire portion to be changed so that an intensity of the induced electric field becomes lager than that of a surrounding region of the magnetic stimulation-target region.

According to the method of manufacturing the coil apparatus for use in the transcranial magnetic stimulation apparatus of the eighth aspect of the present invention, in the method of manufacturing the coil apparatus for use in the transcranial magnetic stimulation apparatus of the seventh aspect of the present invention, the method further including the step of: setting the distance between the near-head-surface conductive wire portion and the far-head-surface conductive wire portion to be changed so that inductance of the coil apparatus falls within a predetermined inductance range and the induced electric field falls within a predetermined spread on the head surface.

According to the ninth aspect of the present invention, there is provided a method of manufacturing a transcranial magnetic stimulation apparatus including the coil apparatus for use in the transcranial magnetic stimulation apparatus of any one of the first to fourth aspects of the present invention, and a drive circuit that outputs a current pulse having a predetermined pulse width to the coil apparatus. The method includes the step of: setting the pulse width to fall within a predetermined pulse width range; and setting a distance between the near-head-surface conductive wire portion and the far-head-surface conductive wire portion to be changed so that an intensity of the induced electric field becomes larger than that of a surrounding region of the magnetic stimulation-target region.

INDUSTRIAL APPLICABILITY

As described above in detail, the present invention can further increase the electric field intensity on the head surface. The present invention can be widely applied to a coil apparatus for use in a transcranial magnetic stimulation apparatus, a method of manufacturing the coil apparatus for use in a transcranial magnetic stimulation apparatus, a transcranial magnetic stimulation apparatus using the coil apparatus, and a method of manufacturing the transcranial magnetic stimulation apparatus.

DESCRIPTION OF REFERENCE CHARACTERS

1: TRANSCRANIAL MAGNETIC STIMULATION SYSTEM
2: STIMULATION COIL
4: CABLE
6: MAGNETIC STIMULATION CONTROL APPARATUS
20: COIL DRIVE CIRCUIT
21: POWER SUPPLY APPARATUS
21a: AC POWER SUPPLY
21b: POWER SUPPLY CIRCUIT
21c: VOLTAGE BOOSTER CIRCUIT
22: CAPACITOR
23: SEMICONDUCTOR SWITCH
23a: THYRISTOR
23b: DIODE
24: INDUCTANCE COMPONENT OF STIMULATION COIL
25: RESISTANCE COMPONENT OF STIMULATION COIL
26: CONTROL CIRCUIT
M: PATIENT

What is claimed is:

1. A coil designing method for designing a coil apparatus including a wound-wire coil configured to be disposed on or near a head surface so as to generate a current by an induced electric field through electromagnetic induction in a magnetic stimulation-target region of a brain for stimulating neurons, wherein the wound-wire coil is a dome-type coil including a near-head-surface conductive wire portion configured to be disposed on or near the head surface and having a cross-section corresponding to and facing a portion of the head surface, and a far-head-surface conductive wire portion configured to be disposed farther from the head surface than the near-head-surface conductive wire portion, wherein the coil designing method comprises:
setting a coil height, which is a maximum value of a distance between the near-head-surface conductive wire portion and the far-head-surface conductive wire portion in the dome-type coil, to make an intensity of the induced electric field in the magnetic stimulation-target region corresponding to the cross-section of the near-head-surface conductive wire portion to be larger than that of a surrounding region which surrounds the magnetic stimulation-target region, by searching for an optimum value of the coil height while maintaining a spread of the induced electric field on the head surface constant by using a constant area of the cross-section of the near-head-surface conductive wire portion of the dome-type coil.

2. The coil designing method as claimed in claim 1, wherein the coil designing method further comprises:
setting the coil height so that an inductance of the coil apparatus falls within a predetermined inductance range and the spread of the induced electric field falls within a predetermined spread on the head surface.

3. The coil designing method as claimed in claim 2, wherein the predetermined inductance range is set to be equal to or larger than 5 μH and equal to or smaller than 13 μH.

* * * * *